(12) United States Patent
Jordan et al.

(10) Patent No.: US 12,051,508 B2
(45) Date of Patent: *Jul. 30, 2024

(54) PREDICTING RESPONSE TO IMMUNOTHERAPY TREATMENT USING DEEP LEARNING ANALYSIS OF IMAGING AND CLINICAL DATA (71) Applicant: ONC.AI, INC., San Carlos, CA (US)

(72) Inventors: Petr Jordan, Emerald Hills, CA (US); Rita Ciaravino, Grosse Pointe Farms, MI (US); Salmaan Ahmed, Kelowna (CA)

(73) Assignee: Onc.ai, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/103,146

(22) Filed: Jan. 30, 2023

(65) Prior Publication Data
US 2023/0178242 A1 Jun. 8, 2023

Related U.S. Application Data (63) Continuation of application No. 17/383,649, filed on Jul. 23, 2021, now Pat. No. 11,568,992.

(51) Int. Cl.
G16H 50/20 (2018.01)
G06N 3/04 (2023.01)
(Continued)

(52) U.S. Cl.
CPC .............. G16H 50/20 (2018.01); G06N 3/04 (2013.01); G06N 3/08 (2013.01); G06T 7/0016 (2013.01);
(Continued)

(58) Field of Classification Search
CPC ........ G16H 50/20; G16H 20/10; G16H 20/40; G16H 30/20; G16H 30/40; G16H 50/30;
(Continued)

(56) References Cited

U.S. PATENT DOCUMENTS 10,575,774 B2    3/2020  Madabhushi et al.
10,950,351 B2 *  3/2021  Madabhushi .......... G16H 50/30
(Continued)

OTHER PUBLICATIONS

Xu, Y. et al. (Apr. 22, 2019). "Deep Learning Predicts Lung Cancer Treatment Response from Serial Medical Imaging," Clinical Cancer Research, 25(11):3266-3275.
(Continued)

Primary Examiner — Robert A Sorey
Assistant Examiner — Kimberly A. Sass
(74) Attorney, Agent, or Firm — Womble Bond Dickinson (US) LLP (57) ABSTRACT A method includes uniquely training, using a processing device, one or more deep learning models using one or more sets of training data associated with a plurality of patients to predict immunotherapy treatment responses indicative of a patient survival rate based on a change in volume of a lesion of a patient. The method includes providing a single pretreatment image of a target lesion of a target patient to the one or more deep learning models that are uniquely trained using the sets of training data to generate the immunotherapy treatment responses. The method includes combining the immunotherapy treatment responses of the one or more deep learning models that are uniquely trained using the sets of training data to generate a predicted treatment response score.

31 Claims, 5 Drawing Sheets

Related U.S. Application Data (60) Provisional application No. 63/056,393, filed on Jul. 24, 2020.

(51) Int. Cl.
| | | |
|---|---|---|
| *G06N 3/08* | (2023.01) | |
| *G06T 7/00* | (2017.01) | |
| *G16H 20/10* | (2018.01) | |
| *G16H 20/40* | (2018.01) | |
| *G16H 30/20* | (2018.01) | |
| *G16H 30/40* | (2018.01) | |
| *G16H 50/30* | (2018.01) | |
| *G16H 50/50* | (2018.01) | |
| *G16H 50/70* | (2018.01) | |

(52) U.S. Cl.
CPC ............. *G16H 20/10* (2018.01); *G16H 20/40* (2018.01); *G16H 30/20* (2018.01); *G16H 30/40* (2018.01); *G16H 50/30* (2018.01); *G16H 50/50* (2018.01); *G16H 50/70* (2018.01); *G06T 2200/04* (2013.01); *G06T 2207/20081* (2013.01); *G06T 2207/20084* (2013.01)

(58) Field of Classification Search
CPC .......... G16H 50/50; G16H 50/70; G06N 3/04; G06N 3/08; G06N 3/044; G06N 3/045; G06N 5/01; G06N 20/10; G06N 3/084; G06N 20/20; G06T 7/0016; G06T 2200/04; G06T 2207/20081; G06T 2207/20084; G06T 2207/30061; G06T 2207/30096

See application file for complete search history.

(56) References Cited

U.S. PATENT DOCUMENTS

| | | | |
|---|---|---|---|
| 2017/0263023 A1* | 9/2017 | Zhou | G06T 11/008 |
| 2018/0242906 A1 | 8/2018 | Madabhushi et al. | |
| 2019/0164642 A1 | 5/2019 | Hartung et al. | |
| 2019/0286790 A1* | 9/2019 | Kaigala | G16B 40/20 |
| 2020/0069973 A1* | 3/2020 | Lou | G16H 30/20 |
| 2020/0114004 A1* | 4/2020 | Tuli | A61N 5/1031 |
| 2020/0258223 A1* | 8/2020 | Yip | G06T 7/11 |

OTHER PUBLICATIONS

Traverso, PhD, A. et al. (Nov. 20, 2017). "Repeatability and Reproducibility of Radiomic Features: A Systematic Review," International Journal of Radiation Oncology, 102(4):1143-1158.

Kim, H. et al. (Apr. 17, 2018). "Effect of CT Reconstruction Algorithm on the Diagnostic Performance of Radiomics Models: A Task-Based Approach for Pulmonary Subsolid Nodules," 212:505-512.

Khorrami, M. et al. (Nov. 12, 2019). "Changes in CT Radiomic Features Associated with Lymphocyte Distribution Predict Overall Survival and Response to Immunotherapy in Non-Small Cell Lung Cancer," American Associates for Cancer Research, pp. 35.

Anonymous: "Deep learning", Wikipedia, Jul. 16, 2020 (Jul. 16, 2020), pp. 34.

Cho, Steve Y. et al.: "Prediction of Response to Immune Checkpoint Inhibitor Therapy Using Early-Time-Point 18 F-FDG PET/CT Imaging in Patients with Advanced Melanoma", The Journal of Nuclear Medicine, 58(9), Mar. 30, 2017 (Mar. 30, 2017), pp. 1421-1428.

Transmittal of the International Search Report and Written Opinion of the International Searching Authority mailed on Nov. 9, 2021, for International Application No. PCT/US2021/042979, filed Jul. 23, 2021, pp. 13.

Office Action for Japanese Patent Application No. 2023-505383, mailed on May 13, 2024.

* cited by examiner

PREDICTING RESPONSE TO IMMUNOTHERAPY TREATMENT USING DEEP LEARNING ANALYSIS OF IMAGING AND CLINICAL DATA

CROSS-REFERENCE TO RELATED APPLICATIONS

This application is a continuation of U.S. patent application Ser. No. 17/383,649, filed Jul. 23, 2021, which claims the benefit of U.S. Provisional Patent Application No. 63/056,393, filed on Jul. 24, 2020, the contents of which are hereby incorporated by reference in their entirety.

TECHNICAL FIELD

The present disclosure relates to predicting immunotherapy treatment response using deep learning analysis, and in particular to systems and methods for predicting responses to PD-[L]1 and CTLA-4 immune checkpoint inhibitors using deep learning analysis of imaging and clinical data.

BRIEF DESCRIPTION OF THE DRAWINGS

The present disclosure will be understood more fully from the detailed description given below and from the accompanying drawings of various implementations of the disclosure.

DETAILED DESCRIPTION

Embodiments of the present invention relate to the field of predicting immunotherapy treatment using deep learning analysis, and in particular to systems and methods for predicting responses to PD-[L]1 and CTLA-4 immune checkpoint inhibitors using deep learning analysis of imaging and clinical data.

Immunotherapy has transformed cancer treatment with the PD-1 (programmed cell death-1) and CTLA-4 (anti-cytotoxic T lymphocyte antigen-4) class of checkpoint inhibitors (e.g., pembrolizumab, nivolumab, atezolizumab, ipilimumab, tremelimumab), demonstrating durable responses in Stage IV metastatic tumors such as non-small cell lung cancer and melanoma. However, unpredictable and low patient response rates coupled with high drugs costs and serious toxicities can significantly burden healthcare systems, third-party payers and patients. Clearly, diagnostic tools to stratify patients according to response likelihood are necessary as PD-[L]1 and CTLA-4 checkpoint inhibitors continue to gain adoption. Recent efforts exploring the utility of quantitative imaging biomarkers to predict response to PD-[L]1 and CTLA-4 immunotherapy have shown promise.

However, despite these numerous successes, PD-1/PD-L1 and CTLA-4 checkpoint blockade therapies do have a number of shortcomings: low response rates, generally in the 15% to 20% range in most diseases when used a single agent, high therapy cost globally ($150,000 or more per year in the United States) and serious immune mediated adverse events. As described above, unpredictable and low patient response rates coupled with high drugs costs and serious toxicities can significantly burden healthcare systems, third-party payers and patients.

Numerous approaches to predict response to PD-1/PD-L1 and CTLA-4 checkpoint therapy have been investigated with limited success. In one embodiment, an immunohistochemistry (IHC) test measures levels of the PD-L1 protein expressed in tumor samples. Tumor mutational burden, presence of Tumor Infiltrating Lymphocytes and inflammatory cytokines are being explored in multiple clinical trials involving PD-[L]1 often in combination with additional immuno-oncology (TO) therapies, such as CTLA-4 checkpoint inhibitors.

In some embodiments, efforts exploring the utility of quantitative imaging biomarkers to predict response to PD-[L]1 immunotherapy may have promise. In such an approach, a non-invasive imaging scan may provide insight and information on the patient's entire tumor burden rather than a sample of a subset of lesions (as provided by biopsy or serum-based assays). When diagnostic images that depict all treatable lesions are further analyzed with computational techniques such as machine-learning and artificial intelligence, resulting in the identification of relevant imaging features, an accurate overall assessment of patient response to PD-[L]1 and/or CTLA-4 therapy may be attainable.

Advantageously, the embodiments provided herein overcome the above and other problems by describing a multi-omic classifier to predict responses to PD-1/PD-L1 and CTLA-4 checkpoint blockade in various clinical indications, including but not limited to non-small cell lung cancer (NSCLC), melanoma, bladder cancer, and breast cancer. In one embodiment, the classifier is developed from training data that includes diagnostic imaging scans at baseline and follow-up intervals, along with existing biomarkers, relevant clinical, molecular, demographic, response and survival data. Examples of existing biomarkers used in clinical practice include: PD-L1 expression immunohistochemistry, tumor mutation burden (TMB), mutation mismatch repair (MMR), microsatellite instability (MSI), and neutrophil-to-lymphocyte ratio (NLR). Furthermore, there is early evidence suggesting that laboratory tests, such as Lactate Dehydrogenase (LDH), S100 proteins and related blood serum proteins are predictive of immunotherapy response and pseudoprogression, specifically. In the near future, features and biomarkers extracted from the microbiome are expected to play a significant role as well.

A high-level sequence of methods of one embodiment of the present disclosure is summarized below: once sufficient patient data are de-identified & accumulated, imaging data (both baseline and follow-up scans) is annotated (segmented) to delineate lesions, lymph nodes, surrounding organs, etc.; clinical notes and other computational metrics (change in tumor volume) are annotated to generate (Response Evaluation Criteria in Solid Tumours) RECIST score in order to assess the response or disease progression at each lesion and at patient level; a pre-processing layer normalizes imaging data based on reconstruction kernel, hardware parameters (CT scanner slice width); and a multi-layered Convolution Neural Network (CNN) processes annotated imaging data along with clinical cohort characteristics.

In one embodiment, the terms "target," "target lesion," "target subject," etc. may refer to a nodule, lesion, tumor, metastatic mass or an anatomical structure near (within some defined proximity to) a treatment area. In another embodiment, a target may be a bony structure or bone metastasis. In yet another embodiment, a target may refer to soft tissue of a patient. A target may be any defined structure or area capable of being identified and tracked (including the entirety of the patient themselves) as described herein.

Furthermore, although PD-1 and CTLA-4 are frequently referred to for convenience and brevity, the embodiments disclosed herein are similarly suitable for any other method of treatment, including but not limited to other forms of immunotherapy, chemotherapy, and radiation therapy. Furthermore, PACS, as used herein, refers to Picture Archiving and Communication System and DICOM refers to Digital Imaging and Communications in Medicine.

Figure 1:
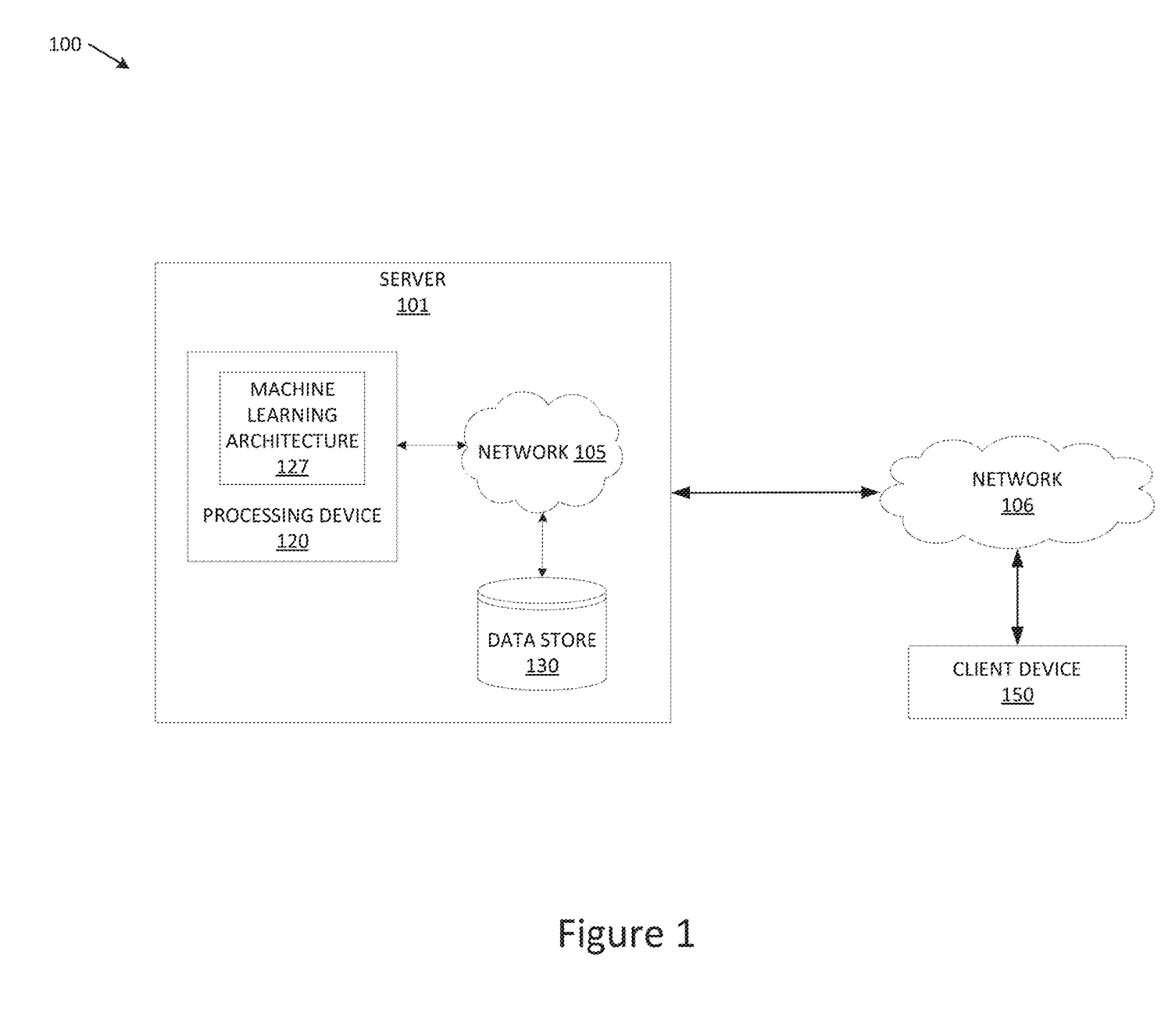
FIG. 1 is a diagram showing a machine learning system for use with embodiments of the present disclosure.

FIG. 1 is a diagram showing a machine learning system 100 for use with embodiments of the present disclosure. Although specific components are disclosed in machine learning system 100, it should be appreciated that such components are examples. That is, embodiments of the present invention are well suited to having various other components or variations of the components recited in machine learning system 100. It is appreciated that the components in machine learning system 100 may operate with other components than those presented, and that not all of the components of machine learning system 100 may be required to achieve the goals of machine learning system 100.

In one embodiment, system 100 includes server 101, network 106, and client device 150. Server 100 may include various components, which may allow for predicting responses to PD-1 checkpoint blockades (and other immunotherapy treatments) using deep learning analysis and of imaging and clinical data on a server device or client device. Each component may perform different functions, operations, actions, processes, methods, etc., for a web application and/or may provide different services, functionalities, and/or resources for the web application. Server 100 may include machine learning architecture 127 of processing device 120 to perform operations related to using trained models to predicting responses to PD-1 checkpoint blockades using deep learning analysis and of imaging and clinical data. In one embodiment, processing device 120 one or more graphics processing units of one or more servers (e.g., including server 101). Additional details of machine learning architecture 127 are provided with respect to the remaining figures of the present disclosure. Server 101 may further include network 105 and data store 130.

The processing device 120 and the data store 130 are operatively coupled to each other (e.g., may be operatively coupled, communicatively coupled, may communicate data/messages with each other) via network 105. Network 105 may be a public network (e.g., the internet), a private network (e.g., a local area network (LAN) or wide area network (WAN)), or a combination thereof. In one embodiment, network 105 may include a wired or a wireless infrastructure, which may be provided by one or more wireless communications systems, such as a Wi-Fi hotspot connected with the network 105 and/or a wireless carrier system that can be implemented using various data processing equipment, communication towers (e.g. cell towers), etc. The network 105 may carry communications (e.g., data, message, packets, frames, etc.) between the various components of server 101. The data store 130 may be a persistent storage that is capable of storing data. A persistent storage may be a local storage unit or a remote storage unit. Persistent storage may be a magnetic storage unit, optical storage unit, solid state storage unit, electronic storage units (main memory), or similar storage unit. Persistent storage may also be a monolithic/single device or a distributed set of devices.

Each component may include hardware such as processing devices (e.g., processors, central processing units (CPUs), graphics processing units (GPUs), memory (e.g., random access memory (RAM), storage devices (e.g., hard-disk drive (HDD), solid-state drive (SSD), etc.), and other hardware devices (e.g., sound card, video card, etc.). The server 100 may comprise any suitable type of computing device or machine that has a programmable processor including, for example, server computers, desktop computers, laptop computers, tablet computers, smartphones, set-top boxes, etc. In some examples, the server 101 may comprise a single machine or may include multiple interconnected machines (e.g., multiple servers configured in a cluster). The server 101 may be implemented by a common entity/organization or may be implemented by different entities/organizations. For example, a server 101 may be operated by a first company/corporation and a second server (not pictured) may be operated by a second company/corporation. Each server may execute or include an operating system (OS), as discussed in more detail below. The OS of a server may manage the execution of other components (e.g., software, applications, etc.) and/or may manage access to the hardware (e.g., processors, memory, storage devices etc.) of the computing device.

As discussed herein, the server 101 may provide machine learning functionality to a client device (e.g., client device 150). In one embodiment, server 101 is operably connected to client device 150 via a network 106. Network 106 may be a public network (e.g., the internet), a private network (e.g., a local area network (LAN) or wide area network (WAN)), or a combination thereof. In one embodiment, network 106 may include a wired or a wireless infrastructure, which may be provided by one or more wireless communications systems, such as a Wi-Fi hotspot connected with the network 106 and/or a wireless carrier system that can be implemented using various data processing equipment, communication towers (e.g. cell towers), etc. The network 106 may carry communications (e.g., data, message, packets, frames, etc.) between the various components of system 100. Further implementation details of the operations performed by system 101 are described with respect to the remaining figures of the present disclosure.

In one embodiment, the system 101 may operate on any of the following data, as well as any other suitable data contemplated.

| Type | Format | Location | Description |
| --- | --- | --- | --- |
| Baseline CT scan of patient | DICOM | PACS | CT scan of patient prior to receiving Tx (slice thickness ≤5 mm, acquired within 6 months of starting IO therapy, including annotations (how many lesions and where) |

-continued

| Type | Format | Location | Description |
|---|---|---|---|
| Follow-up CT scan(s) | DICOM | PACS | Follow-up CT, PET/CT and relevant diagnostic studies (e.g. MRI, X-ray) |
| Clinical Features | XLS, CSV, HL7/FHIR | PACS and EHR SYSTEM | Gender<br>Ethnicity<br>Age<br>IO therapy administration schedule (start date, end date, dose history, other concurrent therapies) w.r.t. baseline and follow-up scans<br>TNM status<br>Clinical biomarkers (PD-L1 immunohistochemistry, TMB, MMR, MSI. Labs (e.g. serum proteins, LDH, S100, neutrophil counts, lymphocyte counts, . . .)<br>Genomic tests<br>ICD10 Code |
| Clinical Performance/Outcome | XLS, CSV, HL7/FHIR | EHR SYSTEM | Disease progression status at each follow-up<br>Time to progression<br>Survival data<br>Immune-related adverse events (irAEs) |

Figure 2:
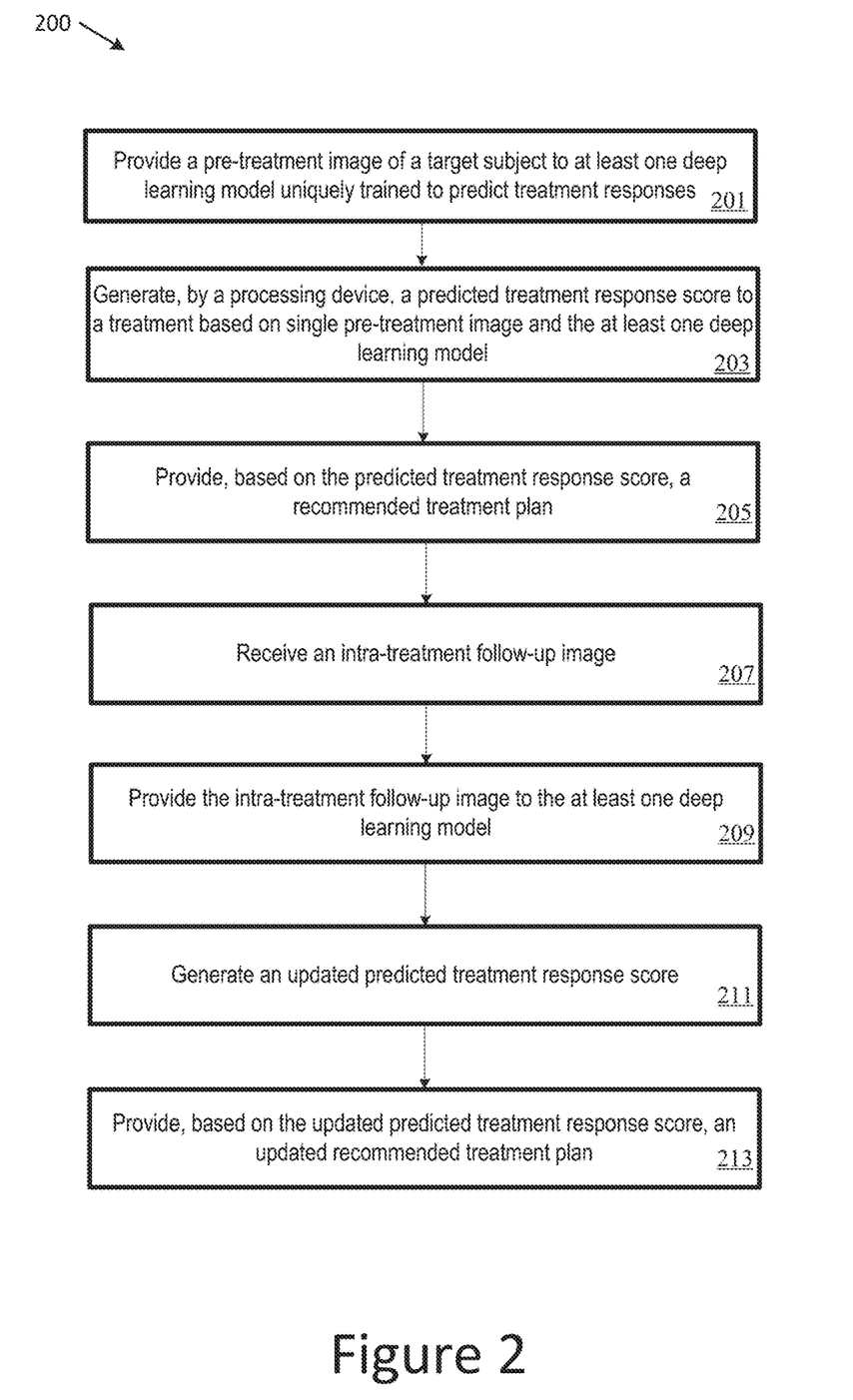
FIG. 2 depicts a flow diagram of a method of predicting immunotherapy treatment using deep learning analysis, in accordance with embodiments of the disclosure.

FIG. 2 depicts a flow diagram of a method of predicting immunotherapy treatment using deep learning analysis, in accordance with embodiments of the disclosure. In general, each of the methods described herein (including method 200) may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the methods may be performed by processing logic of the machine learning architecture 127 of FIG. 1.

Method 200 begins with processing logic at block 201 providing a pre-treatment image of a target subject, optionally including lesion annotations or seed points, to at least one deep learning model uniquely trained to predict treatment responses (e.g., immunotherapy treatment) based on a single lesion or multiple lesions. In embodiments, other types of machine learning models may be used instead of or in conjunction with the at least one deep learning model. In some embodiments, a large set of predefined imaging and clinical features is generated, followed by a feature selection algorithm (e.g. minimum redundancy maximum relevance (MRMR) or least absolute shrinkage and selection operator (LASSO)), and fitted using machine learning methods (e.g. gradient boosted decision trees, random decision forests, or support vector machines) to produce a predictive model. The optional lesion annotations or seed points provided to block 201 may be generated manually by the clinical user or automatically by an autosegmentation and/or target detection method. An example of automatic autosegmentation or target detection method is a convolutional neural network model. To predict treatment response of a single lesion, a model is trained using multiparametric optimization techniques, such as stochastic gradient descent (SGD), RMSprop, or adaptive momentum (Adam) algorithms, to maximize the agreement between model-predicted lesion response and lesion response determined by human expert (e.g. radiologist).

Examples of lesion response may include, numerical assessment (e.g. change in lesion volume, change in one or more primary dimensions of the lesion, change in image intensity within the lesions), tumor growth rate (TGR), or categorical assessment (e.g. responding lesion, stable lesion, progressing lesion, new lesion). Predicting treatment response at patient level is performed by aggregating one or more lesion-level model predictions. In one embodiment, aggregation from lesion to patient level response prediction is performed by a set of rules and logical operations.

In embodiments, a per-lesion response score may be calculated for multiple lesions in a single patient, followed by a mathematical operation, such as maximum score, minimum score, and/or mean score to transform the multiple per-lesion response predictions into a single, patient-level response prediction. In an embodiment, aggregation from lesion to patient level response prediction is performed by a second model, which takes predictions from one or more lesion-level models as an input and is trained specifically to perform patient-level response prediction. In some embodiments, to account for variable numbers of lesions (e.g., the model inputs), the inputs into the model may be the lesion-level prediction statistics (e.g., mean, median, standard deviation, etc.). In another embodiment, the model may be a recurrent neural network (RNN) model in which multiple lesion predictions are represented as an input sequence of variable length.

Examples of patient-level model include, but are not limited to, artificial neural network, random forest model, support vector machine, and logistic regression model. In another embodiment, a single machine learning model may be used that considers multiple lesions at once. Such an embodiment may effectively remove the hierarchy of per-lesion and per-patient models. In one embodiment, the pre-treatment image may be a two-dimensional anatomical image, a three-dimensional anatomical image, or a four-dimensional anatomical image. In another embodiment, two or more treatment images of a variety of types may be used.

The treatment image may be taken at the time of diagnosis (prior to start of treatment) or during any other suitable time. The treatment image may be, but is not limited to, a computed tomography (CT) scan, a positron emission tomography (PET) scan, or a magnetic resonance imaging (MM) scan. The at least one deep learning model may include any suitable variety of machine learning models including, but not limited to, a convolutional neural network. In one embodiment, the models are trained on same data, using different hyper-parameters and optimization techniques. In another embodiment, the models are trained on different data, using different techniques, have different objectives, etc., the results of which may be aggregated in a variety of ways.

The deep learning models may utilize a variety of suitable training methods. For example, in one embodiment, the deep learning models use a population of training subjects and a plurality of images associated with each of a plurality of training subjects as training data. In another embodiment, the deep learning models use calculated subject-specific models as training data. In yet another embodiment, the deep learning models use a combination of the two methods described above.

In embodiments, the treatment is a PD-[L]1 immune checkpoint inhibitor treatment. The PD-[L]1 immune checkpoint inhibitor treatment may be a PD-1-based treatment or a PD-L1-based treatment. In yet another embodiment, the treatment is a CTLA-4-immune checkpoint inhibitor treatment, or any other suitable treatment type (e.g., chemotherapy, targeted therapy, pharmaceutical-based therapy, radiotherapy, etc.).

At block 203, processing logic generates (e.g., by a processing device) a predicted treatment response score (e.g., on a scale representing least likely to have a positive of negative effect to most likely to have a positive or negative effect) to an immunotherapy treatment based on the deep learning models. In some embodiments, the predicted treatment response score may be a numerical value. In one embodiment, processing logic generates the predicted treatment response score based on the single pre-treatment image and the at least one deep learning model. For example, in one embodiment, results from the different models may be combined (e.g., averaged, or combined in any other way) to generate a single response score. In one embodiment, one or more non-imaging features (e.g., genomic tests, electronic medical record information, PD-L1 immunohistochemistry assays, etc.) may be used to generate the predicted response score. In another embodiment, the one or more non-imaging features may be combined with one or more imaging features to generate the predicted response score.

In one embodiment, the predicted treatment response score includes a prediction of patient progression on a predefined pharmaceutical product. In another embodiment, the predicted treatment response score indicates a prediction of one or more immune-related adverse events associated with the immunotherapy treatment. In one embodiment, the predicted treatment response score may include a predicted likelihood (e.g., a confidence level) of a specific type of response and/or adverse event occurring. In another embodiment, the response score may also include an indication of pseudo-progression, which is characterized by short-term and temporary increase in tumor volume due to natural swelling and/or inflammation (e.g., in response to treatment), rather than progression of disease. In another embodiment, the response score may reflect the likelihood of hyper-progression, which is a serious condition associated with rapid clinical deterioration and in which progression of disease is accelerated during administration of therapy. In another embodiment, the response score may be formulated to indicate progression-free or overall patient survival in units of months or years.

At block 205, processing logic provides, based on the predicted treatment response, a recommended treatment plan. For example, based on the predicted treatment response, a recommended treatment plan may include an indication of whether a specific pharmaceutical product should be used, a dosage of such product, a timing associated with administering such a product, etc. In embodiments, the indication may identify whether or not a patient is likely to respond to the specific pharmaceutical product. In one embodiment, the per-lesion immunotherapy and/or chemotherapy response predictions are used to generate a lesion-specific therapy plan to enhance the therapeutic effect in high-risk lesions by combining ongoing systemic therapy with localized therapy. Localized therapy may be any of the following: stereotactic ablative radiation therapy (SBRT), intensity modulated radiation therapy (IMRT), conformal radiation therapy (CRT), radiosurgery, surgical resection, thermal ablation, cryoablation, or high intensity focused ultrasound (HIFU) therapy. In another embodiment, the recommended treatment plan for a patient with a model-predicted high risk of progression may be to add chemotherapy or CTLA-4 immunotherapy in combination with PD-[L]1 immunotherapy to maximize treatment response likelihood. In another embodiment, the recommended treatment plan may be to discontinue one or all therapeutic methods to maximize patient's quality of life. In embodiments, the processing logic may generate other outputs based on the predicted treatment response score instead of or in conjunction with a recommended treatment plan. For example, the processing logic may generate a report based on the predicted treatment response score.

At block 207, the processing logic may receive an intra-treatment follow-up image.

At block 209, the processing logic may provide the intra-treatment follow-up image to the machine learning model.

At block 211, the processing logic may generate an updated predicted treatment response score.

At block 213, the processing logic may provide, based on the updated predicted treatment response score, an updated recommended treatment plan.

In a variety of embodiments, processing logic may perform any number of suitable pre- and post-processing operations that may increase the accuracy, efficiency, and/or compatibility of the machine learning model in the context at hand. For example, with respect to preprocessing, traditional radiomics methods may be susceptible to variations in scanner hardware and imaging protocols. The data preprocessing and data augmentation systems described herein are designed to optimize model generalizability and to minimize model susceptibility to imaging hardware and protocol variations.

In the field of machine learning and deep learning specifically, there are known strategies for improving model generalizability. For each category, the following methods, and others, are contemplated:

1. Selecting model size (parameter count) that achieves optimal balance between underfitting and overfitting available training data. A) MLops (e.g., machine learning and operations) framework and infrastructure allows for the monitoring of model key performance indicators (KPIs) and for continually adjusting model complexity and architecture as more data is acquired.

2. Maximizing training dataset diversity. A) Training data may be sourced from diverse institutions (academic, small community centers, and large payer/provider networks), reflecting varying clinical practice trends and diverse imaging hardware and radiology protocols (for example, some community cancer centers use CT protocols with thicker 5 mm slices, while research institutions tend to use high-resolution, 1-2 mm, thin slice scans). B) Training data may be internally cataloged using a database system and ensured proper distribution of imaging hardware and protocols when training models.

3. Input data normalization. A) During model training and model inference, scans may be resampled to consistent resolution (for example, this may be 1.0×1.0×1.0 mm voxel spacing). This significantly reduces model performance dependence on CT slice thickness. B) Image voxel intensities may be normalized by excluding intensity outliers (metal artifacts from fiducials, pacemakers, wires, etc.) and rescaling the intensities to a consistent range (e.g. intensity distribution with 0 mean and variance of 1). C) In cases where multiple reconstructions protocols are available for a given imaging session, reconstruction protocol most consistent with a "gold standard" protocol may be used.

4. Augmenting training data by generating synthetic training examples that simulate feasible scenarios not represented in available training data. A) Online augmentation strategy may be used, which means that new variations of training data are continually generated as long as the model is being trained. In practice, this means that the number of unique training examples is infinite and is only limited by time spent in the model training loop. Online augmentation loops perform model shifts, rotations, rescaling operations, deformations, and intensity perturbations to generate new, unique training cases. B) Physics-based principles may be used to generated noise and intensity variations to simulate differences between scanner hardware and scanning protocols. Examples of physics-based methods include raytracing and Monte-Carlo photon simulations on existing clinical CT scans to generate variations of CT projection data, which can subsequently be used to reconstruct new CT scans with alternate imaging protocols and simulated artifacts. Examples of simulated artifacts include different primary beam energies, beam scatter and hardening characteristics, patient motion artifacts, imaging dose variations.

5. Model inputs using multiple resolutions and region-of-interest (ROI) sizes. A) The CNN model may prefer a subregion (ROI) of one or more CT scans as an input. ROIs of varying size and resolution may be used to create a redundant representation of the input CT image (or subregion) in the vicinity of the tumor location. By using multiple ROI sizes, the model can accommodate for tumors of different size and shape. For example, if only an ROI spanning 5×5×5 cm around the tumor was used, the model would likely not perform well on large tumors. Conversely, if a 50×50×50 cm ROI was used, the classifier would likely not perform well for smaller tumors that require high spatial resolution and fidelity. Combining ROI regions with small and large spatial dimensions in one model facilitates complementary learning of imaging features at the local context (e.g. tumor shape, texture, and intensity profile) and at the global context (e.g. location of the lesion within the body and with respect to other organs, lymph node involvement, patient's body mass composition and muscle reserve, overall health or vital organs, microcalcifications, etc.) and may ultimately results in more predictive and more robust treatment response and survival prediction models.

With respect to post-processing, a variety of techniques may be used to post-process individual model predictions to obtain the predictions accuracy and explainability required by clinical end users. Examples of post processing methods used may include, but are not limited to:

1. Model Ensembles: ensembling (or bagging) is a method for improving stability and overall performance of models. Rather than training one model for a given task, multiple variations of a model are trained (by perturbing training hyper parameters, weight initializations, model architecture, training set distribution, etc.). The multiple models are then used simultaneously by calculating a consensus among them (ensemble prediction). In one embodiment, an average or median prediction from multiple models is on average more accurate than a single prediction. Examples of ensembling operations to combine multiple model predictions can be simple averaging, median calculating, the STAPLE algorithm (Simultaneous Truth and Performance Level Estimation, Warfield et. al.), or a dedicated ensembling model, such as linear classifier, random forest, support vector machine, or a neural network.

2. Bottom-up model aggregation: In some clinical applications, the concept of training a classification model for predicting single lesion response to a therapeutic agent may be desirable. In some clinical scenarios, the clinical requirement is to predict treatment response at the patient level (i.e. Will this patient benefit from given therapy overall, considering that some lesions may respond while others will continue to progress?). In this scenario, the concept of model ensembles may also be applicable. In this application, however, each single-lesion model (or sub-ensemble of models) contributes to the overall patient-level prediction, which is estimated by ensembling individual lesion predictions. Combining the prediction of each model within the larger ensemble and incorporating other clinical factors, biomarkers, and/or imaging features, processing logic can make predictions of treatment response at the patient level, rather than lesion level.

3. Explainability: The response of a deep convolutional network model can be broken down into activations of dominant features to highlight which spatial, textural, and morphologic features most influenced the prediction. For example, the explanation may predict "high risk of lesion progression" due to: 1. lesion volume greater than 50 cc, 2. lesion location in the apex of the lung, 3. low textural heterogeneity at the core and the perimeter of the lesion, 4. presence of metastatic bone lesions. In a related embodiment, model response prediction or a prediction of immune-related adverse events may be explained and supported by the processing unit by presenting reference data and historical cases of patients with similar presentation and medical history profiles.

Incorporating of Temporal Information: In one embodiment, the treatment prediction model can be thought of as either a "single shot" prediction at baseline that determines the future course of treatment, or as a continually integrated process that incorporates imaging and electronic medical record (EMR) information along the course of the treatment, providing continuous decision support for the clinician. In one embodiment, a treatment response model is trained to predict patient's likelihood of disease progression, pseudo-progression, or hyper-progression using baseline and first intra-treatment follow-up scan. In this clinical scenario, the model prediction may be used to significantly reduce the timeline to make treatment decision or adjustment, such as moving patient to a different therapeutic agent, adding a secondary therapeutic agent, or discontinuing therapy. In the case of prediction models which incorporate multiple imaging time points, temporal data can be integrated in various ways (two imaging time points may be used for illustration purposes):

1. Approach #1: Calculating the difference in imaging features between scan #1 and scan #2, which are subsequently used to create a prediction model. In one embodiment, sets of imaging features may be calculated independently for scan #1 and scan #1. The feature weights or values calculated from scan #1 may be subtracted from the features or values calculated from scan #2. The difference or changes in the individual features may constitute a set of new "delta features" that corresponds to temporal variations in typical image features (e.g., change in shape, intensity, texture, etc. as a function of time).

2. Approach #2: Training a 4D CNN prediction model with input ROI shape being $[N_x, N_y, N_z, 2]$, where $N_x$, $N_y$, $N_z$ are the number of voxels along each axis and 2 corresponds to two (or more) imaging time points, each represented with a single 3D volume within the 4D input volume). This approach is similar to multi-modal CNN models. The most obvious being natural images in RGB format, where each color channel is represented separately. In our case, each channel is used for representing one event in time.

3. Approach #3: Calculating the intensity difference between spatially registered scans #1 and #2 and subsequently training a 3D CNN prediction model (model input ROI shape being $[N_x, N_y, N_z, 1]$, where $N_x$, $N_y$, $N_z$ are the number of voxels along each axis and 1 corresponds to single intensity channel).

4. Approach #4: Training a model combining 3D CNN with RNN (recurrent neural network), where the RNN is used to model sequence of imaging inputs.

Figure 3A:
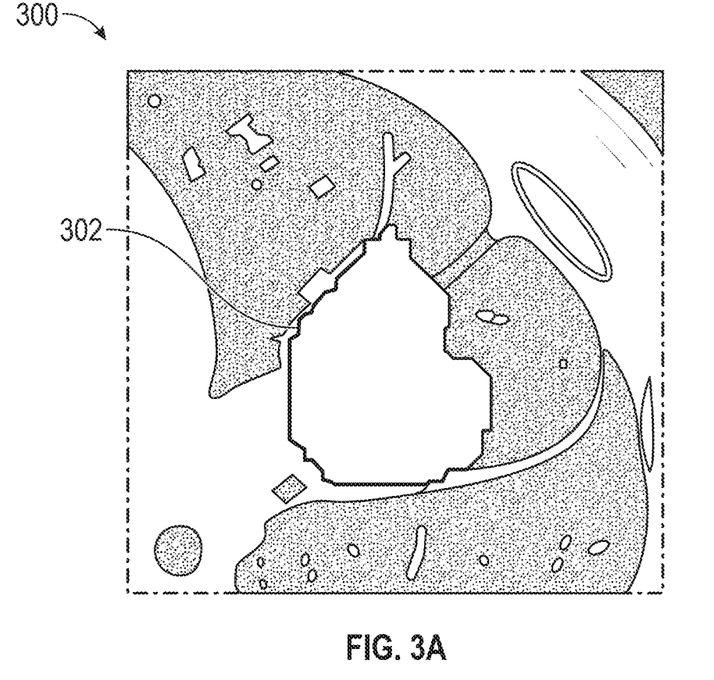
FIG. 3A is an illustration of an example of a pre-treatment image of a target, in accordance with embodiments of the disclosure.

FIG. 3A is an illustration of an example of a pre-treatment image 300 of a target, in accordance with embodiments of the disclosure. Pre-treatment image 300 may correspond to the pre-treatment image as previously described at FIG. 2. The pre-treatment image 300 may correspond to a lung lesion 302 of a patient during a baseline scan. In embodiments, the baseline scan may be performed on the patient prior to receiving therapy. In embodiments, the pre-treatment image 300 may correspond to a CT image. In some embodiments, the pre-treatment image 300 may correspond to a PET image. In an embodiment, the pre-treatment image 300 may correspond to an MRI image. In some embodiments, other types of pre-treatment images may be used.

Figure 3B:
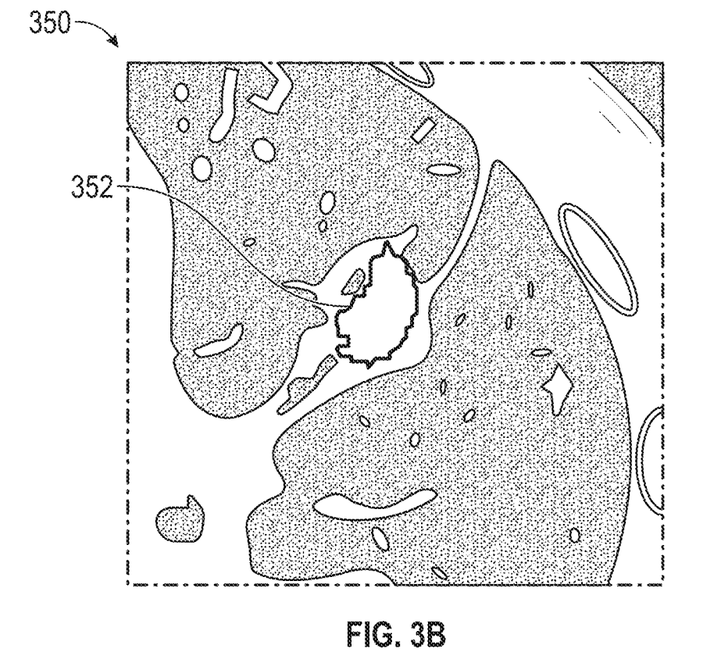
FIG. 3B is an illustration of an example of a follow-up image of a target, in accordance with embodiments of the disclosure.

FIG. 3B is an illustration of an example of a follow-up image 350 of a target, in accordance with embodiments of the disclosure. As previously described, embodiments of the disclosure may utilize one or more follow-up images, such as follow-up image 350, of the target that were captured after treatment. The follow-up image 350 includes lung lesion 352, which may correspond to lung lesion 302 after receiving treatment. In embodiments, the follow-up image 350 may be provided to the machine learning architecture 127 and may be used to determine whether the current treatment plan is effective and should continue, whether there is a more effective treatment option, and/or whether the treatment should be discontinued based on an analysis of the follow-up image 350 relative to pre-treatment image 300. In embodiments, the follow-up image 350 may correspond to a CT image. In some embodiments, the follow-up image 350 may correspond to a PET image. In an embodiment, the follow-up image 350 may correspond to an MM image. In some embodiments, other types of follow-up images may be used.

Figure 4:
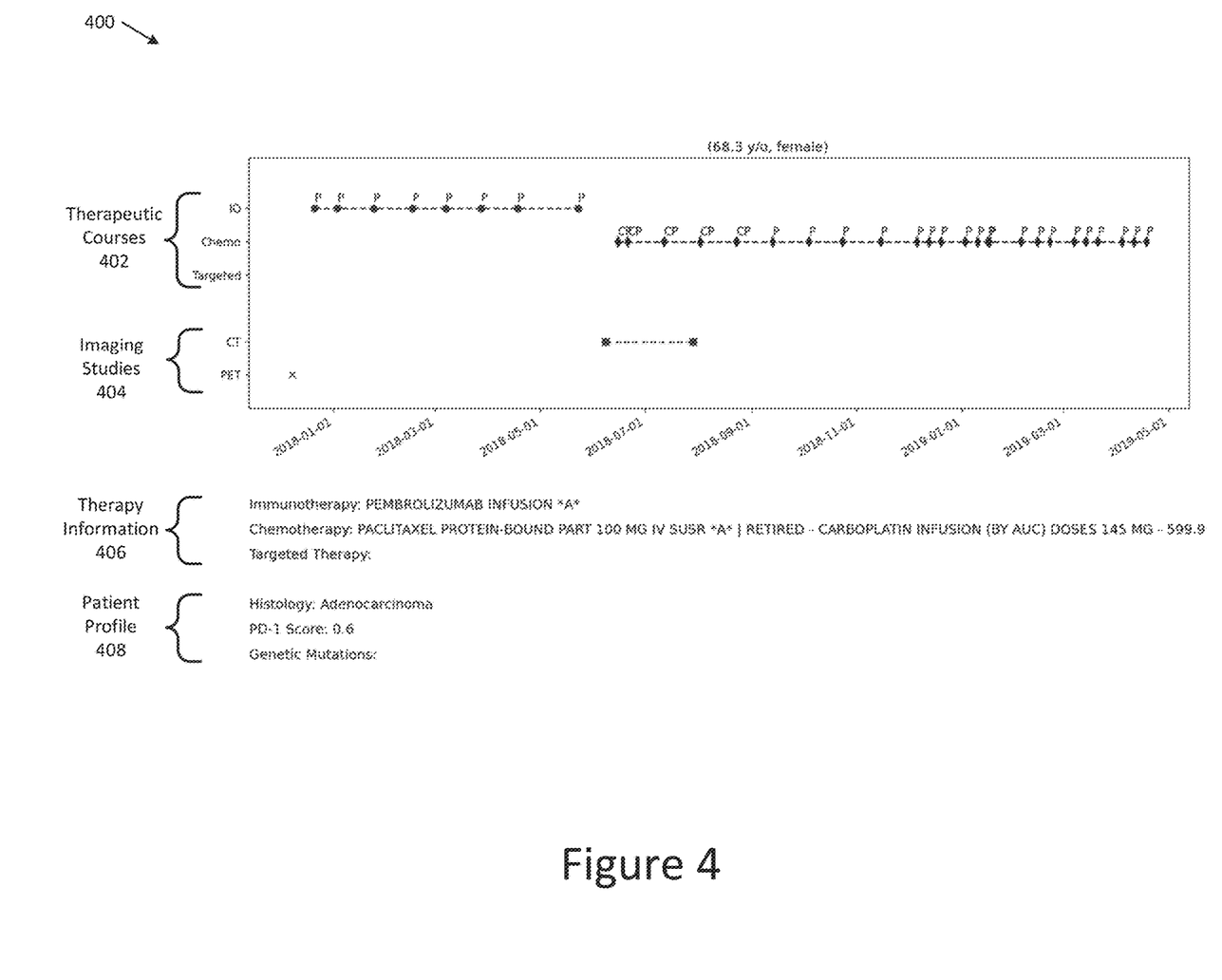
FIG. 4 is an illustration of an example of an output that is generated based on the predicted treatment response score, in accordance with embodiments of the disclosure.

FIG. 4 is an illustration of an example of an output 400 that is generated based on the predicted treatment response score, in accordance with embodiments of the disclosure. In embodiments, output 400 may be generated based on a predicted treatment response score, as previously described. The output 400 illustrates a temporal relationship between therapeutic courses 402 (e.g., immunotherapy, chemotherapy, targeted therapy) and imaging studies 404 (e.g., CT and PET imaging). The output 400 may indicate when the different therapeutic courses 402 and/or imaging studies 404 are to be administered relative to a treatment timeline.

The output 400 may also include therapy information 406. The therapy information 406 may indicate which types of immunotherapy, chemotherapy, and/or targeted therapy are recommended to use in treatment. The output 400 may further include patient profile 408 that includes information associated with the patient receiving treatment. Examples of information included in the patient profile 408, may include, but are not limited to, patient age, patient gender, known genomic driver mutations, PD-L1 immunohistochemistry tissue proportion score (TPS), or the like.

It should be noted that output 400 is shown for illustrative purposes only and is not meant to limit the present disclosure. Embodiments of the disclosure may generate other types of outputs based on a predicted treatment response score that may vary in appearance and/or the information (e.g., therapeutic courses 402, imaging studies 404, therapy information 406, patient profile 408) relative to output 400 provided in FIG. 4.

Figure 5:
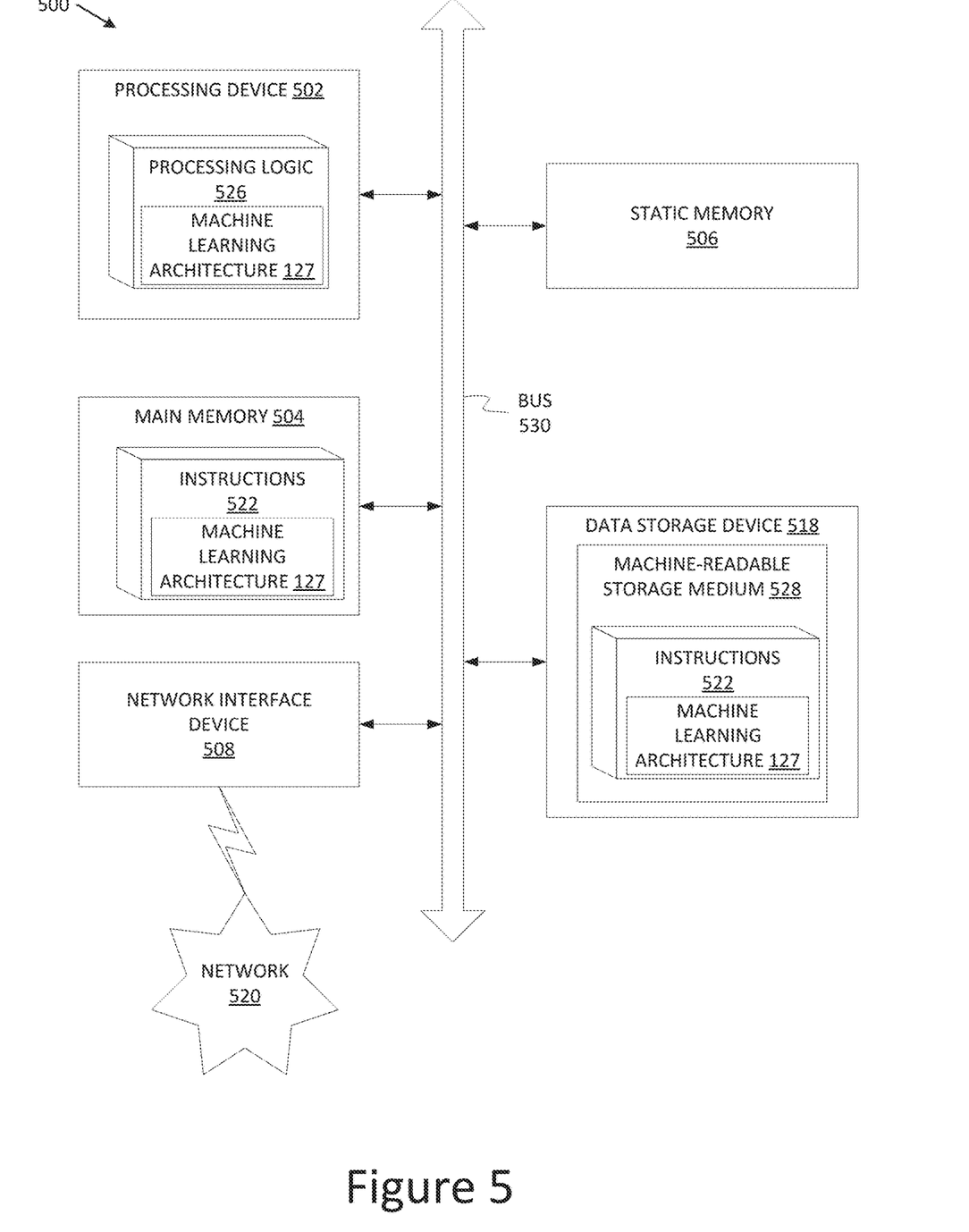
FIG. 5 illustrates examples of different systems that may be used to predict immunotherapy treatment using deep learning analysis, in accordance with embodiments described herein.

FIG. 5 illustrates a diagrammatic representation of a machine in the example form of a computer system 500 within which a set of instructions 522, for causing the machine to perform any one or more of the methodologies discussed herein, may be executed. In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, a switch or bridge, a hub, an access point, a network access control device, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. In one embodiment, computer system 500 may be representative of a server computer system, such as system 100.

The exemplary computer system 500 includes a processing device 502, a main memory 504 (e.g., read-only memory (ROM), flash memory, dynamic random access memory (DRAM), a static memory 506 (e.g., flash memory, static random access memory (SRAM), etc.), and a data storage device 518, which communicate with each other via a bus 530. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Processing device 502 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 502 may also be one or more special-purpose processing devices such as an application specific integrated circuit (ASIC), a field programmable gate array (FPGA), a digital signal processor (DSP), network processor, or the like. The processing device 502 is configured to execute processing logic 526, which may be one example of system 100 shown in FIG. 1, for performing the operations and steps discussed herein.

The data storage device 518 may include a machine-readable storage medium 528, on which is stored one or more set of instructions 522 (e.g., software) embodying any one or more of the methodologies of functions described herein, including instructions to cause the processing device 502 to execute system 100. The instructions 522 may also reside, completely or at least partially, within the main memory 504 or within the processing device 502 during execution thereof by the computer system 500; the main memory 504 and the processing device 502 also constituting machine-readable storage media. The instructions 522 may further be transmitted or received over a network 520 via the network interface device 508.

The machine-readable storage medium 528 may also be used to store instructions to perform the methods and operations described herein. While the machine-readable storage medium 528 is shown in an exemplary embodiment to be a single medium, the term "machine-readable storage medium" should be taken to include a single medium or multiple media (e.g., a centralized or distributed database, or associated caches and servers) that store the one or more sets of instructions. A machine-readable medium includes any mechanism for storing information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Additionally, some embodiments may be practiced in distributed computing environments where the machine-readable medium is stored on and or executed by more than one computer system. In addition, the information transferred between computer systems may either be pulled or pushed across the communication medium connecting the computer systems.

Embodiments of the claimed subject matter include, but are not limited to, various operations described herein. These operations may be performed by hardware components, software, firmware, or a combination thereof.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

It will be appreciated that variants of the above-disclosed and other features and functions, or alternatives thereof, may be combined into may other different systems or applications. Various presently unforeseen or unanticipated alternatives, modifications, variations, or improvements therein may be subsequently made by those skilled in the art which are also intended to be encompassed by the following claims. The claims may encompass embodiments in hardware, software, or a combination thereof. In the foregoing specification, the disclosure has been described with reference to specific exemplary implementations thereof. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense.

What is claimed, is:

1. A method, comprising:
   uniquely training, using a processing device, one or more deep learning models using one or more sets of training data associated with a plurality of patients to predict immunotherapy treatment responses indicative of a patient survival rate based on a change in volume of a lesion of a patient, wherein each of the sets of training data are indicative of at least one of unique diagnostic imaging scans at baselines, follow-up intervals, or temporary changes in lesion volume;
   providing a single pre-treatment image of a target lesion of a target patient to the one or more deep learning models that are uniquely trained using the sets of training data to generate the immunotherapy treatment responses; and
   combining the immunotherapy treatment responses of the one or more deep learning models that are uniquely trained using the sets of training data to generate a predicted treatment response score.

2. The method of claim 1, further comprising:
receiving an intra-treatment follow-up image;
providing the intra-treatment follow-up image to the at least one deep learning model;
generating an updated predicted treatment response score; and
providing, based on the updated predicted treatment response score, an updated recommended treatment plan.

3. The method of claim 1, wherein the pre-treatment image comprises a plurality of imaging features.

4. The method of claim 1, wherein the at least one deep learning model comprises a convolutional neural network.

5. The method of claim 1, wherein the treatment is a PD-[L]1 immune checkpoint inhibitor treatment.

6. The method of claim 1, wherein the treatment is a PD-[L]1 or CTLA-4-immune checkpoint inhibitor treatment.

7. The method of claim 1, wherein the treatment is a PD-[L]1-based treatment or CTLA-4-based treatment combined with chemotherapy treatment.

8. The method of claim 1, wherein the treatment is a PD-[L]1-based treatment or CTLA-4-based treatment combined with radiotherapy treatment.

9. The method of claim 1, wherein the pre-treatment image is one of: a three-dimensional anatomical image or a four-dimensional anatomical image.

10. The method of claim 1, wherein the at least one deep learning model use a population of training subjects and a plurality of images associated with each of a plurality of training subjects as training data.

11. The method of claim 1, wherein the predicted treatment response score indicates a prediction of a response to a predefined pharmaceutical product.

12. The method of claim 1, wherein the predicted treatment response score indicates a prediction of a progression-free survival at patient-level and lesion-level on a predefined pharmaceutical product.

13. The method of claim 1, wherein the predicted treatment response score indicates a prediction of an overall survival at a patient-level and lesion-level on a predefined pharmaceutical product.

14. The method of claim 1, wherein the predicted treatment response score indicates a prediction of hyper-progression at a patient-level and lesion-level on a predefined pharmaceutical product.

15. The method of claim 1, wherein the immunotherapy treatment responses are further indicative of a disease control.

16. The method of claim 1, wherein the predicted treatment response score indicates a prediction of one or more immune-related adverse events associated with the treatment.

17. The method of claim 1, further comprising:
providing, to the at least one deep learning model, one or more non-imaging features associated with the target subject, wherein the predicted treatment response score to the treatment is generated based on the single pre-treatment image, the one or more non-imaging features, and the at least one deep learning model.

18. A treatment analysis system comprising:
a memory to store a pre-treatment image of a target subject; and
a processing device, operatively coupled to the memory, the processing device to:
uniquely train one or more deep learning models using one or more sets of training data associated with a plurality of patients to predict immunotherapy treatment responses indicative of a patient survival rate based on a change in volume of a lesion of a patient, wherein each of the sets of training data are indicative of at least one of unique diagnostic imaging scans at baselines, follow-up intervals, or temporary changes in lesion volume;
provide a single pre-treatment image of a target lesion of a target patient to the one or more deep learning models that are uniquely trained using sets of training data to generate the immunotherapy treatment responses; and
combine the immunotherapy treatment responses of the one or more deep learning models that are uniquely trained using the sets of training data to generate a predicted treatment response score.

19. The treatment analysis system of claim 18, wherein the at least one deep learning model comprises a convolutional neural network.

20. The treatment analysis system of claim 18, wherein the treatment is a PD-[L]1 immune checkpoint inhibitor treatment.

21. The treatment analysis system of claim 18, wherein the treatment is a PD-[L]1 or CTLA-4-immune checkpoint inhibitor treatment.

22. The treatment analysis system of claim 18, wherein the treatment is a PD-[L]1-based treatment or CTLA-4-based treatment combined with chemotherapy treatment.

23. The treatment analysis system of claim 18, wherein the immunotherapy treatment responses are further indicative of a disease control.

24. The treatment analysis system of claim 18, wherein the predicted treatment response score indicates a prediction of hyper-progression at a patient-level and lesion-level on a predefined pharmaceutical product.

25. A non-transitory computer-readable storage medium comprising instructions, which when executed by a processing device, cause the processing device to:
uniquely train, using the processing device, one or more deep learning models using one or more sets of training data associated with a plurality of patients to predict immunotherapy treatment responses indicative of a patient survival rate based on a change in volume of a lesion of a patient, wherein each of the sets of training data are indicative of at least one of unique diagnostic imaging scans at baselines, follow-up intervals, or temporary changes in lesion volume;
provide a single pre-treatment image of a target lesion of a target patient to the one or more deep learning models that are uniquely trained using sets of training data to generate the immunotherapy treatment responses; and
combine, by the processing device, the immunotherapy treatment responses of the one or more deep learning models that are uniquely trained using the sets of training data to generate a predicted treatment response score.

26. The non-transitory computer-readable storage medium of claim 25, wherein the at least one deep learning model comprises a convolutional neural network.

27. The non-transitory computer-readable storage medium of claim 25, wherein the treatment is a PD-[L]1 immune checkpoint inhibitor treatment.

28. The non-transitory computer-readable storage medium of claim 25, wherein the treatment is a PD-[L]1 or CTLA-4-immune checkpoint inhibitor treatment.

29. The non-transitory computer-readable storage medium of claim 25, wherein the treatment is a PD-[L]1-based treatment or CTLA-4-based treatment combined with chemotherapy treatment.

30. The non-transitory computer-readable storage medium of claim 25, wherein the predicted treatment response score indicates a prediction of hyper-progression at a patient-level and lesion-level on a predefined pharmaceutical product.

31. The non-transitory computer-readable storage medium of claim 25, wherein the immunotherapy treatment responses are further indicative of a disease control.

* * * * *